United States Patent [19]

Ohlenschläger et al.

[11] 4,081,682
[45] Mar. 28, 1978

[54] LOCATING AND IDENTIFYING A RADIOACTIVE URANIUM AND/OR TRANSURANIUM ISOTOPE DEPOSITED IN A WOUND

[75] Inventors: Lothar Ohlenschläger, Eggenstein-Leopoldshafen; Olaf Fromhein, Bruchsal; Wilhelm Rapp, Eggenstein-Leopoldshafen, all of Germany

[73] Assignee: Gesellschaft fur Kernforschung m.b.H., Karlsruhe, Germany

[21] Appl. No.: 747,684

[22] Filed: Dec. 6, 1976

[30] Foreign Application Priority Data

Dec. 5, 1975 Germany ............................ 2554668

[51] Int. Cl.$^2$ ............................................. G01T 1/20
[52] U.S. Cl. ................................. 250/362; 250/363 R; 250/369; 250/393
[58] Field of Search ................. 250/361 R, 369, 370, 250/374, 393, 312, 362; 128/1.1

[56] References Cited

PUBLICATIONS

A Miniaturized Probe for Detecting Radioactivity at Thyroid Surgery, Morris et al., Phys. Med. Biol., 1971, vol. 16, No. 3, pp. 397–404.

Avalanche Detector Arrays for In Vivo Measurement of Plutonium and Other Low Activity, Low Energy Emitter, IEEE Trans. Nucl. Sci. 19 (1972), No. 1.

*Primary Examiner*—Davis L. Willis
*Attorney, Agent, or Firm*—Spencer & Kaye

[57] ABSTRACT

A method and apparatus for accurately locating and roughly identifying a radioactive uranium and/or transuranium isotope deposited in a wound, by monitoring alpha radiation in the edge region of the wound and at the wound surface to determine whether surface contamination is present, monitoring low-energy X-ray or gamma radiation at the wound to determine the presence of a low-energy X-ray or gamma radiation source, measuring the low-energy X-ray or gamma radiation in the wound by means of a succession of detectors having progressively increasing local resolution and progressively decreasing limitation of the detectable volume to effect coarse and then fine localization of even small isotope deposits. An isotope can be roughly identified by displaying the measuring result produced by at least one of the detectors as a pulse amplitude spectrum, and comparing the displayed result with subsequently measured spectra of predetermined isotopes.

13 Claims, 2 Drawing Figures

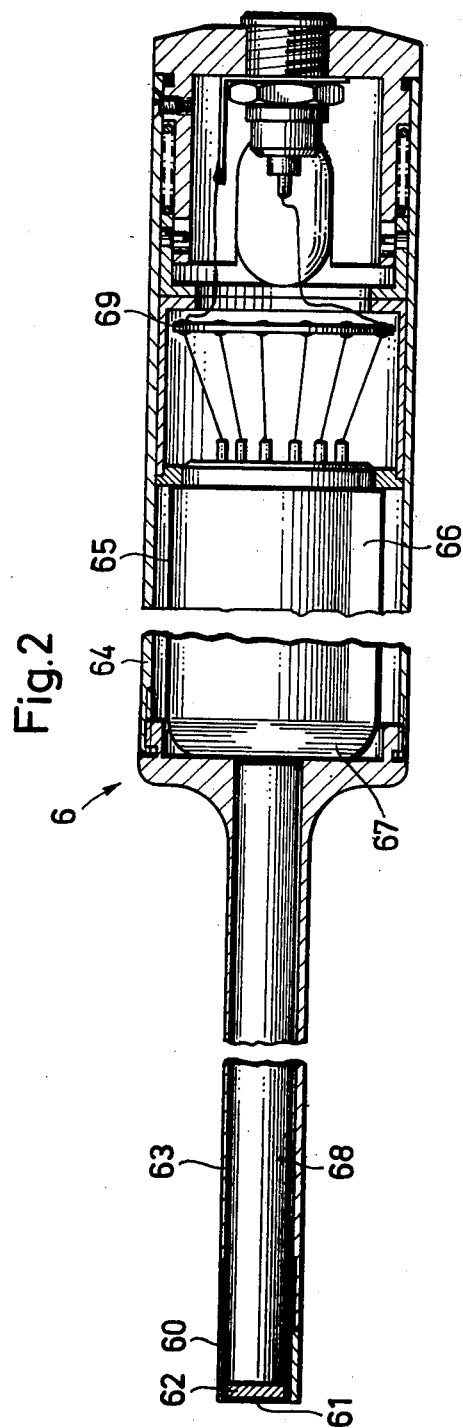

LOCATING AND IDENTIFYING A RADIOACTIVE URANIUM AND/OR TRANSURANIUM ISOTOPE DEPOSITED IN A WOUND

BACKGROUND OF THE INVENTION

The present invention relates to a wound measuring method and apparatus for locating and roughly identifying a radioactive uranium and/or transuranium isotope deposited in a wound.

The use of radioactive isotopes is greatly increasing in many areas of science and technology so that a constantly increasing number of people is subject to the risk of accidents resulting in radioactively contaminated injuries. Of particular importance in this connection are long-lived, highly radiotoxic radionuclides which occur predominantly in industries which process nuclear fuels and in the reprocessing of nuclear fuels.

The number of accidents leading to contaminated wounds is relatively small compared to conventional injuries but these accidents do require particular medical attention because the resorption of radioactive material through opened lymph and blood vessels includes the danger of incorporation in, and thus damage to, the entire organism. This applies in particular for the long-lived and radiotoxic isotopes of the transuranium elements which are known to concentrate in bone tissue.

Detection of such radionuclides in a wound is possible only by measuring their radiation by means of suitable detectors since even quantities too small to be weighed constitute radiation-biological limit values.

The surgical procedure employed in the treatment of a contaminated injury depends on the type and extent of the injury as well as on the level, spread and type of radioactivity, and on the location of the deposit in the wound.

Problems are encountered in measuring the alpha radiation from the deposit in the wound since such radiation travels only a short distance, for example for plutonium 239 only about 40$\mu$ with an energy of 5 MeV, due to absorption of the radiation by tissue, wound secretion and coagulation.

Beta or gamma radiation is not difficult to measure since the absorption of such radiation in the body tissues is significantly lower. For that reason the low energy X-ray or gamma radiation occurring in alpha radiators is used to detect a radioactive deposit in a wound. This is disclosed in the periodical Strahlentherapie [Radiation Therapy] 146, 4 (1973), at pages 422–432.

In this known measuring process the low-energy X-ray and gamma radiation is measured by means of scintillation counters. A particular drawback thereof is that for structural reasons the detectors have such dimensions that the measurements can be effected only on the surface of the skin but not in the wound itself. The surgical procedure required to remove the radioactive deposit in the wound, however, must be substantially restricted in its spatial extent.

This presupposes that it is possible to locate the deposit in the wound as precisely as possible. The more imprecisely the location is determined, the greater must be the area of tissue operated on, in order to increase the chances of success, and this often includes otherwise unnecessary amputations. Thus, in the interest of maintaining the health and the full work capacity of the patient, it is urgently necessary to limit the surgical operation to the absolutely necessary area.

It has therefore been proposed, for example, in IEEE Trans. Nucl. Sci 19 (1972) No. 1; and IEEE Trans. Nucl. Sci 20 (1973) No. 1, to utilize semiconductor detectors for tissue measurements, i.e., measurements in the wound. However, semiconductor detectors are not suitable as means for precisely localizing a low energy emitting deposit in a wound because the temperature noise of the semiconductor detector in the range of the body temperature is so strong that it substantially masks the measured radiation signal. Moreover, since the probability that the semiconductor detector will produce a positive response is relatively low, i.e. there is a good likelihood that any given wound will not contain a deposit, measuring times in the order of magnitude of several minutes would be required. However, long measuring times are contrary to the requirement of giving the patient medical attention in the shortest possible time in order to avoid substantial damage.

Another drawback of semiconductor detectors is the relatively high operating voltage, of the order of magnitude of 1000 volts, which constitutes a potential danger from a medical point of view when used in the area of a wound.

It is also known, as disclosed in Phys. Med. Biol. vol. 16 (1971) No. 3, at pp. 397–404, from the field of nuclear medicine to use scintillation detectors to detect precisely known radioactive preparations which have been administered to the patient. The CsI (Tl) crystal used for this purpose is, however, too insensitive for measuring low energy beta and gamma radiation. The collimator which is placed on the head of the probe would preclude use of the detector in a wound due to its diameter of 14 mm.

SUMMARY OF THE INVENTION

It is therefore an object of the present invention to locate radioactive isotopes of uranium or of transuranium elements in the shortest possible time and with high accuracy and to effect a rough identification of the isotope so that necessary surgical procedures can be limited to the deposit in the wound and its immediate vicinity.

A further object of the invention is to provide a measuring device for carrying out the method and which furnishes all the required information about the location and type of the deposit in the wound to the treating physician, precludes erroneous measurements and is easy to operate so that the physician's efforts can remain substantially directed toward the patient.

These and other objects are accomplished according to the present invention by performing measurements of alpha radiation in the area of the edges of the wound and at the surface of the wound to determine whether surface contamination is present, performing an additional measurement, in the wound, of the low-energy X-ray or gamma radiation to determine whether a low-energy X-ray or gamma radiator is present, then, for the rough or fine location of even the smallest deposits of uranium and/or transuranium isotopes in the wound, measuring the low-energy X-ray or gamma radiation in the wound by the successive use of a choice of different detectors having progressively increasing local resolution and progressively decreasing limitation of the detectable volume, and displaying the measuring result from one or a plurality of partial measurements as a pulse amplitude spectrum and comparing the pulse amplitude spectrum with subsequently measured spectra of predetermined isotopes, for producing a rough identification of the isotope of the radioactive deposit enclosed in the wound.

It has here been found to be particularly advantageous, in the sense of facilitating work and shortening the procedure, for the output signals of the detectors to be converted to audio frequency signals which are used as acoustic orientation aids and the detector pulses which were generated by the radiation of predetermined energy ranges to be converted to acoustic signals of predetermined fixed audio frequencies, and one or a plurality of predetermined audio frequencies are selected, from a plurality of possible audio frequencies. With this arrangement, alignment of the axis of the detector with the deposit in the wound maximizes the number of pulses of the acoustic signal.

The work of the physician can be facilitated, in certain cases, by converting the detector pulses, independently of the energy of the generating radiation, into acoustic signals of one frequency which are used to align the detector, after maximizing the monotonic acoustic signal dividing the energy spectrum into a plurality of energy ranges, with each energy range being assigned a predetermined fixed audio frequency, and using each energy range individually or together with one or a plurality of other energy ranges to localize a deposit in a wound.

With respect to the practice of the method, the goals of the invention are achieved by including in the receiver for the measured values an alpha-beta monitor and a plurality of detectors for low-energy X-ray and gamma radiation whose local resolution capabilities are adapted to one another in a predetermined manner, connecting the detectors to an arrestable of fixable, device, allowing each detector to be connected together in a predetermined arrangement via a control unit, with an electronic measuring value processor, providing means for converting pulses into acoustic signals, permitting each detector to be connected to a multichannel analyzer to receive spectrograms, and providing for connection of an XY plotter and/or printer to record spectrograms.

In this connection, it has been found to be particularly advantageous to combine the components into a mobile unit on a movable table mounting the control unit with the control field for operating the measuring device, the multichannel analyzer and a display for displaying the measured results, to be rotatable about a vertical axis and arrestable, or fixable, in predetermined positions, constituting the apparatus for holding the detectors substantially of a pivot arm rotatable about a vertical axis and inclined with respect to that axis, the upper end of the pivot arm being connected to independently movable arms each having a fork-type mount for a detector and each detector being fully cardanically suspended, the pivot arm and every arm connected thereto being arrestable in a freely selectable predetermined spatial position by means of electromagnets.

The advantages realized by the present invention reside in particular in that even the smallest particles of radioactive material with an activity of 2 nCi which have entered a wound and have there formed a deposit, can be detected as to their location down to a volume of about 20mm$^3$. The time required for locating the deposits is reduced to the order of magnitude of a few minutes. The surgical operation required to remove the radioactive deposit in the wound can be restricted to the immediate vicinity of the deposit since its location has been precisely determined. In borderline cases this can prevent amputations and can substantially exclude complications as a result of radiotoxic material entering the bloodstream. The possibility for rapid rough identification of radiotoxic foreign elements which have entered a wound increases the certainty of the treating physician with respect to his selection of suitable procedures and means. The easy operability of the wound measuring station permits the physician to fully concentrate on his diagnosis and therapy. The possibility of recording the measuring results assures documentary proof of the treatment of the patient.

BRIEF DESCRIPTION OF THE DRAWINGS

FIG. 2 is a longitudinal cross-sectional view of a wound probe employed in the system of FIG. 1.

DESCRIPTION OF THE PREFERRED EMBODIMENTS

Figure 1:
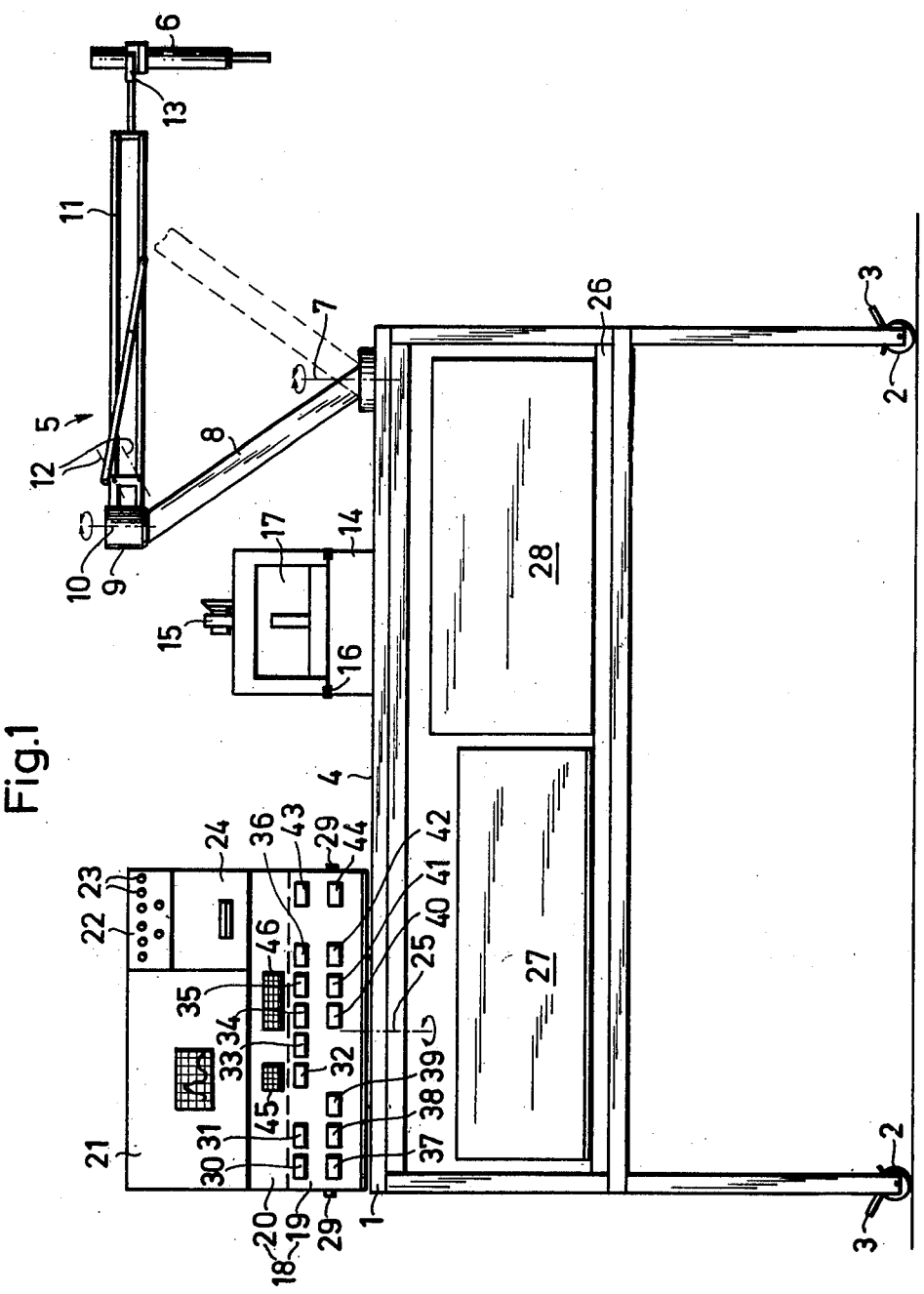
FIG. 1 is a simplified pictorial, elevational view of a wound measuring station according to the invention.

The wound measuring station shown in FIG. 1 for medically diagnosing an injury contaminated with radioactive substances substantially includes a Table 1 which can be moved rollers 2 and blocked by means of clamps 3. A device 5 for holding a plurality of detectors 6 is disposed on the top 4 of Table 1 and includes a pivot arm 8 which is rotatable about a vertical axis 7 and inclined with respect to this axis. Three arms 11 which are rotatable about a vertical axis 10 are connected to the head 9 of the pivot arm 8. These arms 11 can be pivoted up and down about horizontal axes 12 in a freely selectable plane of axis 10. During pivoting of arms 11 about axes 12, these arms remain parallel to one another, constituting a parallelogram linkage which assures that the orientation of fork-shaped half-cardanic mount 13 for accommodating detector 6 is independent of the position of the arm. The movements about axes 7, 10 and 12 can be blocked electromagnetically in predetermined freely selectable positions.

A mount 14 carrying a fixable cardanic, or universal, joint 15 is likewise mounted on top 4 of Table 1 and an alpha-beta radiation monitor 17 can be inserted into rails 16 provided on mount 14.

Table top 4 is further provided with a control unit 18, including a control panel 19 to operate the wound measuring station and a display panel 20 to display the measuring results, a multichannel analyzer 21 to receive the energy spectra signals, a keyboard 22 with switches 23 for selecting predetermined measuring channels and arresting the pivot arms, and a printer 24 for recording the measured values. Components 18-24 are combined into a structural group which can be pivoted through about 270° about a vertical axis 25. An intermediate bottom 26 below table top 4 accommodates an XY plotter 27 which can be pulled out on either sides to record spectrograms, and an electronic measuring value processor 28. On both sides of control unit 18 there are jacks 29 for connecting a headset.

The instruments are arranged on the top 4 of table 1 in a manner to assure that they can be operated easily from either side of the operating table and the physician will have the patient continuously in view even when he is handling the wound measuring station.

To control the wound measuring station, control panel 19 includes a contact key for each function and an associated luminescent panel. One or a plurality of contact keys serving to prepare a function each have a start key associated therewith. Errors are recognized and not performed. The contact switches are formed with high resistance MOS-FET semiconductors for which the transfer resistance of the surface of the skin on the operator's finger constitutes practically a short circuit.

The control panel 19 is equipped with luminescent panels and contact keys for the following functions: alpha-beta radiation monitor, preparation 30, start 31; spectrogram reception, preparation 32; first detector, preparation 33; second detector, preparation 34; third detector, preparation 35, start 36; XY plotter, preparation 37; counting rate determination, preparation 38; printer preparation 39; start channel setting 40; final channel setting 41; start 42, test 43, reset 44.

On the display 45 of display panel 20, the measuring time is indicated in seconds or, if the measured value is recorded, the number of the measuring channel is indicated. For measuring value recording display 46 indicates the contents of the channel displayed in display 45, and for alpha radiation measurement the pulse rate.

With the wound measuring station, the following measurements can be made at and in a radioactively contaminated wound:
1. counting rate measurement with alpha-beta monitor 17 at the surface of the wound;
2. spectrometric measurements at and in the wound with a first NaI, detector (6.1) for energies below 100 keV without particular local resolution, with a second, NaI, detector (6.2) for energies below 60 keV with coarse local resolution, and with a third, NaI, detector (6.3) for energies below 60 keV with fine local resolution;
3. recording of the energy spectrum with an XY plotter 27 and/or printer 24;
4. determinatin of the counting rate within a freely selectable, predetermined energy range.

Commercially available components
1. Alpha-beta-monitor 17: CONTAMAT from Friesecke & Hoepfner, Germany The monitor is fixed in a mechanical support allowing mobile and stationary application.
2. Multichannel analyzer 21: KEVOTRON 250 Schlumberger, Germany
3. Printer 24: SEDELEC TL 21 Schlumberger, Germany
4. XY-Plotter: Servogor xy, RE 551 METRAWATT, Germany The above mentioned components can be replaced by any other equipment with appropriate specification. Most of the interface system (28) and the multichannel function 21 can be replaced by using microprocessors.

Developed components
1. Wound probe 6 is described
2. Electronic interface 28 for control of the instrumentation including voltage supplies, signal preamplifier, filtering and acoustical amplifier for hearing aids.
3. Audio discriminator switches. Discriminator is used as an acoustical aid for wound deposit locating. Principle: Provision of frequency modulated signals with respect to six energy ranges.

All control functions are initiated via the control board 18. In case of alpha-beta-monitoring a touch of the sense button 30 establishes the connection between the monitor 17 and a counter in the interface system 18 which counts the induced pulses within the predetermined measuring time. The result is displayed in display 46. The monitor 17 has been provided with a proper electronic circuit for output matching. With sense button 32 the multichannel analyzer 21 is prepared for histogram measurements. One of the detectors 6 is coupled via its own preamplifier in 28 by touch of the sense button 33, 34, or 35 to the analysis input of 21. The measured spectrum is displayed on the screen of the multichannel analyzer 21 and can be registered on the XY-plotter 27 or printer 24 by sensing the buttons 37 or 39 which means preparing the analyzer 21 and the interface 28 for registration. The sensor 42 initialises the start and provides the pulses for interrogating the addresses of the memory and transferring the XY information via the control board 28 to the plotter 27 or printer 24.

FIG. 2 is a longitudinal cross-sectional view of one embodiment of a detector 6 used as a wound probe in systems according to the invention. At the head of the probe, there is disposed a cup-shaped crystal holder 60 of aluminum whose frontal face is designed as a window 61 and which is sealed by means of an aluminum foil of $50\mu$ thickness. This holder supports, in window 61, a sodium iodide crystal 62 which has been activated with thallium to serve as an energy transducer to convert the low energy X-ray and gamma radiation emanating from the deposit in the wound into light pulses. The decomposition of plutonium 239 develops uranium 235 which emits, with respect to the gamma radiation, about 5% low-energy X-ray and gamma radiation in the energy range from 13 to 21 keV, particularly about 17 keV. The half-life emission travel of the low-energy X-ray and gamma radiation in the cell tissues is about 5mm, and that of the emitted alpha particles only 0.04mm at 5 MeV, so that the detection of alpha radiators is preferably effected by observing the low-energy X-ray and gamma radiation.

The sodium iodide crystal 62 has a thickness of 1mm. The diameter of the disc determines the sensitivity of the probe and is 12mm in the first detector 6.1, 6mm in the second detector 6.2, and 3mm in the third detector 6.3, all three detectors being otherwise identical to that shown in FIG. 2. The local resolution capability is greater the smaller the diameter of the crystal. By exchanging the crystal of 12mm diameter and 1mm thickness for a crystal of 12mm diameter and 12mm thickness, the first detector 6.1 can be used for energies in the range up to 1 MeV. The good local resolution capability of the wound probe is a result particularly of the fact that with the proposed crystal geometry and a distance from the crystal surface of the order of magnitude of the crystal diameter, the sensitivity drops to about 10% of the value present at the crystal surface. If, therefore, detectors 6 with ever decreasing crystal diameters are set with the aid of the headset so that a maximum number of pulses results, the deposit in the wound must lie in a range around the center of the crystal which corresponds to the diameter of the deposit.

The crystal holder 60 adheres to a probe tube 63 which is connected to a sleeve tube 64 of about 23mm in diameter so that it can easily be removed. Sleeve 64 houses a photomultiplier 66 which is magnetically shielded by means of a self-adhering foil 65 of a material sold under the trademark Mumetal. The photocathode 67 of photomultiplier 66 is connected with the scintillator crystal 62 via a rigid light conductor 68. In order to provide better optical coupling, the space between crystal 62, light conductor 68 and photocathode 67 is filled with a silicone oil.

The detector further includes a voltage divider 69 designed as a thick-film resistance network. The preamplifier for the detector is disposed in the electronic measuring value processor 28 of the system shown in FIG. 1. Thus in the interest of better handling, the size and weight of the wound probe is substantially reduced.

At a measuring time of 100 seconds, all detectors 6 have a sensitivity of about 1 nCi for a dot-like plutonium 239 source.

The sterility of the wound probe is assured by the application of a sterile lacquer which hardens in air to form a foil which can be easily removed.

The essential difference between the invention and the prior art detector (Phys. Med. Biol., 1971, Vol. 16, 397–404) is the fact that the invention needs a much more sensitive and even smaller detector for spectrogram analysis. Activity and energy of the applied radioactive material is known and not hazardous for the patient whereas in the invention the pectrogram analysis must be capable of differentiation between various unknown and highly toxic nuclides. Because of the low energy X-ray detection no special provision for directivity improvement is necessary, since the window thickness is about 50 μm against 500 μm wall thickness.

The probe construction is highly optimised with respect to extreme sensitivity (1 nCi in 100 s) and light weight performance.

It will be understood that the above description of the present invention is susceptible to various modifications, changes and adaptations, and the same are intended to be comprehended within the meaning and range of equivalents of the appended claims.

What is claimed is:

1. A method for accurately locating and roughly identifying a radioactive uranium or transuranium isotope deposited in a wound, comprising the steps of: monitoring alpha radiation in the edge region of the wound and at the wound surface to determine whether surface contamination is present; monitoring low-energy X-ray or gamma radiation at the wound to determine the presence of a low-energy X-ray or gamma radiation source; measuring the low-energy X-ray or gamma radiation in the wound by means of a succession of detectors having progressively increasing local resolution and decreasing limitation of the defectable volume to effect coarse and then fine localization of even small uranium or transuranium isotope deposits in a wound; displaying the measuring result produced by at least one of the detectors as a pulse amplitude spectrum; and comparing the displayed result, in order to roughly identify the isotope of the radioactive deposit enclosed in the wound, with subsequently measured spectra of predetermined isotopes.

2. Method as defined in claim 1 wherein said step of measuring comprises converting the output signals of the detectors to audio frequency signals, utilizing the audio frequency signals to align the detectors, converting the detector pulses produced by radiation in predetermined energy ranges into audible signals at predetermined fixed audio frequencies, and selecting at least one predetermined audio frequency from a plurality of possible audio frequencies, whereby alignment of the axis of the detector with the deposit in the wound maximizes the number of pulses of the acoustic signal.

3. Method as defined in claim 2 wherein, in said step of converting the output signals of the detectors, the detector pulses are converted, independently of the energy of the generating radiation, to acoustic signals of one frequency, said utilizing step employes said signals to align the detector, and said steps of converting the detector pulses and selecting are carried out by maximizing the single frequency acoustic signal, dividing energy spectrum into a plurality of energy ranges, with each energy range having assigned to it a predetermined fixed audio frequency, and using each energy range to localize a deposit in a wound.

4. An arrangement as defined in claim 3 wherein said step of using is carried out by considering each range individually.

5. An arrangement as defined in claim 3 wherein said step of using is carried out by considering each range together with at least one other range.

6. Apparatus for accurately locating and roughly identifying a radioactive uranium or transuranium isotope deposited in a wound, comprising: an alpha-beta radiation monitor; a succession of detectors for low-energy X-ray and gamma radiation, having progressively increasing local resolution and decreasing limitation of the detectable volume for effecting coarse and then fine localization of even small uranium or transuranium isotope deposits in a wound; a movable and fixable support device carrying said detectors; an electronic measuring value processor arranged for connection to the output of each said detector; means for converting pulses from said detectors into acoustic signals; a multichannel analyzer arranged for connection to the output of each said detector to record spectrograms; and means connected for recording the spectrogams.

7. An arrangement as defined in claim 6 further comprising: a movable table carrying said monitor, said detectors, said support device, said processor, said means for converting pulses, said analyzer and said means for recording, to constitute a mobile unit; control means connected to control the operation of said apparatus; display means for displaying the measuring results produced by said detectors; and pivotal support means carrying said control means, said display means and said analyzer and arranged to pivot about a vertical axis and to be selectively held stationary in any one of several selected positions.

8. An arrangement as defined in claim 6 wherein said support device comprises: a pivot arm mounted for rotation about a vertical axis and inclined relative to the axis; a plurality of arm members, one for each detector, each connected to the upper end of said arm for independent movement relative to one another; a plurality of mounting forks each connected to a respective arm; and a plurality of universal joint means each connecting a respective detector to its respective fork.

9. An arrangement as defined in claim 8 further comprising electromagnets arranged to hold said pivot arm and each of said arm members in a freely selectable predetermined spatial position.

10. An arrangement as defined in claim 9 further comprising a selector circuit for releasing one said arm member for free movement while simultaneously preventing movement of at least a second one of said arm members.

11. An arrangement as defined in claim 6 further comprising a mount provided with guide rails, said monitor being mounted on said guide rails; and a lockable universal joint carried by said mount.

12. An arrangement as defined in claim 6 wherein each one of the detectors comprises: a photomultiplier; a thick-film voltage divider connected to said photomultiplier; a disc-shaped crystal constituting an energy transducer; and a light conductor connecting said crystal to said photomultiplier; the local resolution capability of said detector being a function of the diameter of the crystal.

13. An arrangement as defined in claim 6 wherein each said detector comprises: an NaI (Tl) crystal constituting an energy transducer; a photomultiplier provided with a photocathode; a light conductor coupling said crystal to said photocathode and forming a pencil-shaped probe with said crystal; means defining a sleeve connected to said probe and containing said photomultiplier; a thick-film voltage divider connected to said photomultiplier and disposed in said sleeve, said detector being arranged to be connected via a cable to a high voltage supply and to transmit its measuring pulses to an external preamplifier.

* * * * *